United States Patent
Hubelbank et al.

(10) Patent No.: US 10,524,851 B2
(45) Date of Patent: Jan. 7, 2020

(54) FINGERSWITCH CIRCUITRY TO REDUCE RF LEAKAGE CURRENT

(71) Applicant: Medtronic Advanced Energy LLC, Minneapolis, MN (US)

(72) Inventors: David Hubelbank, Manchester, NH (US); Jesse A. Smith, Portsmouth, NH (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 780 days.

(21) Appl. No.: 14/928,020

(22) Filed: Oct. 30, 2015

(65) Prior Publication Data
US 2016/0120590 A1     May 5, 2016

Related U.S. Application Data

(60) Provisional application No. 62/164,930, filed on May 21, 2015, provisional application No. 62/073,705, filed on Oct. 31, 2014.

(51) Int. Cl.
    *A61B 18/12*     (2006.01)
    *A61B 18/00*     (2006.01)
    *A61B 18/14*     (2006.01)

(52) U.S. Cl.
    CPC ...... *A61B 18/1233* (2013.01); *A61B 18/1206* (2013.01); *A61B 18/1402* (2013.01);
(Continued)

(58) Field of Classification Search
    CPC ......... A61B 18/08; A61B 18/10; A61B 18/12; A61B 18/1206; A61B 18/1233;
(Continued)

(56) References Cited

U.S. PATENT DOCUMENTS

| 39,358 A | 7/1863 | Smith |
|---|---|---|
| 41,921 A | 3/1864 | Holmes |

(Continued)

FOREIGN PATENT DOCUMENTS

| CN | 102641152 | 3/2014 |
|---|---|---|
| DE | 3420339 | 1/1985 |
| EP | 2474165 | 7/2012 |

OTHER PUBLICATIONS

Valleylab™, Service Manual, Force FX™-8C Electrosurgical Generator with Instant Response™ Technology, Sep. 2000, pp. 1-218.
(Continued)

*Primary Examiner* — Michael F Peffley
*Assistant Examiner* — Khadijeh A Vahdat
(74) *Attorney, Agent, or Firm* — Christopher & Weisberg, P.A.

(57) ABSTRACT

An electrosurgical unit having detection circuitry for reducing radiofrequency leakage current in an electrosurgical unit. The electrosurgical unit includes a radiofrequency generator configured to generate electrosurgical energy, the radiofrequency generator including a detection circuit having a resistor ladder and an isolation transformer in electrical communication with the resistor ladder. The detection circuit is configured to detect a change in impedance across the isolation transformer and correlate the change in impedance to one of a plurality of predetermined energy thresholds.

10 Claims, 3 Drawing Sheets

(52) U.S. Cl.
CPC ..... *A61B 18/148* (2013.01); *A61B 2018/0016* (2013.01); *A61B 2018/00178* (2013.01); *A61B 2018/00607* (2013.01); *A61B 2018/00642* (2013.01); *A61B 2018/00648* (2013.01); *A61B 2018/00666* (2013.01); *A61B 2018/00702* (2013.01); *A61B 2018/00767* (2013.01); *A61B 2018/00827* (2013.01); *A61B 2018/00875* (2013.01); *A61B 2018/00892* (2013.01); *A61B 2018/124* (2013.01); *A61B 2018/126* (2013.01); *A61B 2018/1253* (2013.01); *A61B 2018/1286* (2013.01)

(58) Field of Classification Search
CPC .............. A61B 18/1402; A61B 18/148; A61B 2018/0016; A61B 2018/00178; A61B 2018/00607; A61B 2018/00642; A61B 2018/00648; A61B 2018/00666; A61B 2018/00702; A61B 2018/00767; A61B 2018/00827; A61B 2018/00875; A61B 2018/00892; A61B 2018/124; A61B 2018/1253; A61B 2018/126; A61B 2018/1286
USPC .................................................. 606/33–50
See application file for complete search history.

(56) References Cited

U.S. PATENT DOCUMENTS

| | | | |
|---|---|---|---|
| 404,004 | A | 5/1889 | Hovey |
| 411,004 | A | 9/1889 | Billings |
| 4,473,075 | A | 9/1984 | Rexroth |
| 4,903,696 | A | 2/1990 | Stasx et al. |
| 5,282,799 | A | 2/1994 | Rydell |
| 5,300,068 | A | 4/1994 | Rosar et al. |
| 5,352,868 | A | 10/1994 | Denen et al. |
| 5,438,302 | A | 8/1995 | Goble |
| 5,573,424 | A | 11/1996 | Poppe |
| 5,582,610 | A | 12/1996 | Grossi et al. |
| 5,599,349 | A | 2/1997 | D'Amelio |
| 5,647,869 | A | 7/1997 | Goble et al. |
| 5,669,906 | A | 9/1997 | Grossi et al. |
| 5,766,153 | A | 6/1998 | Eggers et al. |
| 5,785,708 | A * | 7/1998 | Betsill .................. A61B 18/14 128/908 |
| 5,860,975 | A | 1/1999 | Goble et al. |
| 5,888,198 | A | 3/1999 | Eggers et al. |
| 5,944,715 | A | 8/1999 | Goble et al. |
| 6,004,319 | A | 12/1999 | Goble et al. |
| 6,013,076 | A | 1/2000 | Goble et al. |
| 6,015,406 | A | 1/2000 | Goble et al. |
| 6,027,501 | A | 2/2000 | Goble et al. |
| 6,039,734 | A | 3/2000 | Goble |
| 6,056,746 | A | 5/2000 | Goble et al. |
| 6,074,386 | A | 6/2000 | Goble et al. |
| 6,090,106 | A | 7/2000 | Goble et al. |
| 6,093,186 | A | 7/2000 | Goble |
| 6,100,920 | A | 8/2000 | Miller et al. |
| 6,151,381 | A | 11/2000 | Grodzins et al. |
| 6,174,308 | B1 | 1/2001 | Goble et al. |
| 6,197,025 | B1 | 3/2001 | Grossi et al. |
| 6,210,405 | B1 | 4/2001 | Goble et al. |
| 6,228,081 | B1 | 5/2001 | Goble |
| 6,234,178 | B1 | 5/2001 | Goble et al. |
| 6,238,388 | B1 | 5/2001 | Ellman et al. |
| 6,261,286 | B1 | 7/2001 | Goble et al. |
| 6,277,114 | B1 | 8/2001 | Bullivant et al. |
| 6,293,942 | B1 | 9/2001 | Goble et al. |
| 6,298,255 | B1 | 10/2001 | Cordero et al. |
| 6,306,134 | B1 | 10/2001 | Goble et al. |
| 6,322,494 | B1 | 11/2001 | Bullivant et al. |
| 6,325,799 | B1 | 12/2001 | Goble |
| 6,336,926 | B1 | 1/2002 | Goble |
| 6,364,877 | B1 | 4/2002 | Goble et al. |
| 6,385,059 | B1 | 5/2002 | Telefus et al. |
| 6,398,781 | B1 | 6/2002 | Goble et al. |
| 6,416,509 | B1 | 7/2002 | Gobel et al. |
| 6,482,202 | B1 | 11/2002 | Gobel et al. |
| 6,488,678 | B2 | 12/2002 | Sherman |
| 6,491,690 | B1 | 12/2002 | Gobel et al. |
| 6,508,815 | B1 | 1/2003 | Strul et al. |
| 6,544,260 | B1 | 4/2003 | Markel et al. |
| 6,547,786 | B1 | 4/2003 | Goble |
| 6,557,559 | B1 | 5/2003 | Eggers et al. |
| 6,558,379 | B1 | 5/2003 | Batchelor et al. |
| 6,565,560 | B1 | 5/2003 | Gobel et al. |
| 6,565,561 | B1 | 5/2003 | Gobel et al. |
| 6,582,427 | B1 | 6/2003 | Gobel et al. |
| 6,611,141 | B1 | 8/2003 | Schulz et al. |
| 6,723,091 | B2 | 4/2004 | Gobel et al. |
| 6,758,846 | B2 | 7/2004 | Gobel et al. |
| 6,761,716 | B2 | 7/2004 | Kadhiresan et al. |
| 6,808,525 | B2 | 10/2004 | Latterell et al. |
| 6,832,998 | B2 | 12/2004 | Goble |
| 6,843,789 | B2 | 1/2005 | Goble |
| 6,893,435 | B2 | 5/2005 | Goble |
| 6,923,803 | B2 | 8/2005 | Goble |
| 6,929,641 | B2 | 8/2005 | Gobel et al. |
| 6,942,660 | B2 | 9/2005 | Pantera et al. |
| 6,966,907 | B2 | 11/2005 | Goble |
| 6,984,231 | B2 | 1/2006 | Gobel et al. |
| 7,001,380 | B2 | 2/2006 | Goble |
| 7,137,980 | B2 | 11/2006 | Buysse et al. |
| 7,147,637 | B2 | 12/2006 | Goble |
| 7,153,300 | B2 | 12/2006 | Goble |
| 7,195,627 | B2 | 3/2007 | Amoah et al. |
| 7,201,750 | B1 | 4/2007 | Eggers et al. |
| 7,211,081 | B2 | 5/2007 | Goble |
| 7,211,084 | B2 | 5/2007 | Gobel et al. |
| 7,214,224 | B2 | 5/2007 | Goble |
| 7,255,696 | B2 | 8/2007 | Gobel et al. |
| 7,278,994 | B2 | 10/2007 | Goble |
| 7,282,048 | B2 | 10/2007 | Gobel et al. |
| 7,300,436 | B2 | 11/2007 | Penny et al. |
| 7,322,975 | B2 | 1/2008 | Gobel et al. |
| 7,335,199 | B2 | 2/2008 | Gobel et al. |
| 7,344,532 | B2 | 3/2008 | Gobel et al. |
| 7,429,261 | B2 | 9/2008 | Kunis et al. |
| 7,442,191 | B2 | 10/2008 | Hovda et al. |
| 7,491,199 | B2 | 2/2009 | Goble |
| 7,651,513 | B2 | 1/2010 | Teoh et al. |
| 7,674,261 | B2 | 3/2010 | Garito |
| 7,674,263 | B2 | 3/2010 | Ryan |
| 7,699,846 | B2 | 4/2010 | Ryan |
| 7,708,733 | B2 | 5/2010 | Sanders et al. |
| 7,717,910 | B2 | 5/2010 | Goble |
| 7,799,020 | B2 | 9/2010 | Shores et al. |
| 7,850,684 | B2 | 12/2010 | Marshall et al. |
| 7,854,736 | B2 | 12/2010 | Ryan |
| 7,855,727 | B2 | 12/2010 | Adler et al. |
| 7,887,534 | B2 | 2/2011 | Hamel et al. |
| 7,887,536 | B2 | 2/2011 | Johnson et al. |
| 7,896,877 | B2 | 3/2011 | Hall et al. |
| 7,993,332 | B2 | 8/2011 | Gobel et al. |
| 8,002,769 | B2 | 8/2011 | Gobel et al. |
| 8,082,043 | B2 | 12/2011 | Sharkey et al. |
| 8,175,590 | B2 | 5/2012 | Hamel et al. |
| 8,192,424 | B2 | 6/2012 | Woloszko |
| 8,226,680 | B2 | 7/2012 | Wallace |
| 8,241,284 | B2 | 8/2012 | Dycus et al. |
| 8,246,616 | B2 | 8/2012 | Amoah et al. |
| 8,251,989 | B1 | 8/2012 | Newton et al. |
| 8,257,350 | B2 | 9/2012 | Marion |
| 8,273,084 | B2 | 9/2012 | Kunis et al. |
| 8,273,085 | B2 | 9/2012 | Park et al. |
| 8,333,760 | B2 | 12/2012 | Roggan et al. |
| 8,355,799 | B2 | 1/2013 | Marion et al. |
| 8,444,638 | B2 | 5/2013 | Woloszko et al. |
| 8,452,422 | B2 | 5/2013 | Desinger et al. |
| 8,512,340 | B2 | 8/2013 | Easley et al. |
| 8,551,088 | B2 | 10/2013 | Falkenstein et al. |
| 8,562,598 | B2 | 10/2013 | Falkenstein et al. |

(56) References Cited

U.S. PATENT DOCUMENTS

| | | |
|---|---|---|
| 8,568,405 B2 | 10/2013 | Cox et al. |
| 8,574,187 B2 | 11/2013 | Marion |
| 8,579,894 B2 | 11/2013 | Falkenstein et al. |
| 8,597,287 B2 | 12/2013 | Benamou et al. |
| 8,617,151 B2 | 12/2013 | Denis et al. |
| 8,657,817 B2 | 2/2014 | Fischer et al. |
| 8,672,934 B2 | 3/2014 | Benamou et al. |
| 8,685,018 B2 | 4/2014 | Cox et al. |
| 8,696,659 B2 | 4/2014 | Marion |
| 8,747,399 B2 | 6/2014 | Woloszko et al. |
| 8,747,401 B2 | 6/2014 | Gonzalez et al. |
| 8,784,415 B2 | 7/2014 | Malackowski et al. |
| 8,790,335 B2 | 7/2014 | Gilbert |
| 8,801,705 B2 | 8/2014 | Sanders et al. |
| 8,870,866 B2 | 10/2014 | Woloszko |
| 8,900,226 B2 | 12/2014 | Silig et al. |
| 8,915,910 B2 | 12/2014 | Falkenstein et al. |
| 8,920,412 B2 | 12/2014 | Fritz et al. |
| 8,932,291 B2 | 1/2015 | Orszulak |
| 9,008,757 B2 | 4/2015 | Wu |
| 9,066,735 B2 | 6/2015 | Williams |
| 9,095,358 B2 | 8/2015 | Woloszko et al. |
| 9,099,863 B2 | 8/2015 | Smith et al. |
| 9,138,282 B2 | 9/2015 | Marion |
| 2001/0014003 A1 | 8/2001 | Dible |
| 2003/0050633 A1 | 3/2003 | Ellman et al. |
| 2003/0083652 A1 | 5/2003 | Markel |
| 2003/0181964 A1 | 9/2003 | Sharkey et al. |
| 2004/0199175 A1 | 10/2004 | Jaeger et al. |
| 2005/0113820 A1 | 5/2005 | Goble et al. |
| 2005/0177184 A1 | 8/2005 | Easley |
| 2006/0004396 A1 | 1/2006 | Easley et al. |
| 2006/0106375 A1 | 5/2006 | Werneth et al. |
| 2006/0142753 A1 | 6/2006 | Francischelli et al. |
| 2006/0149225 A1 | 7/2006 | McClurken |
| 2007/0073334 A1 | 3/2007 | Rarnzipoor |
| 2007/0083193 A1 | 4/2007 | Werneth et al. |
| 2007/0083195 A1 | 4/2007 | Werneth et al. |
| 2007/0085496 A1 | 4/2007 | Philipp et al. |
| 2007/0104610 A1 | 5/2007 | Houston et al. |
| 2007/0167941 A1 | 7/2007 | Hamel et al. |
| 2007/0225550 A1 | 9/2007 | Gattani et al. |
| 2008/0082095 A1 | 4/2008 | Shores et al. |
| 2008/0108940 A1 | 5/2008 | Sharkey et al. |
| 2008/0281312 A1 | 11/2008 | Werneth et al. |
| 2008/0281322 A1 | 11/2008 | Sherman et al. |
| 2009/0018429 A1* | 1/2009 | Saliga ............... A61B 5/04004 600/407 |
| 2009/0182325 A1 | 7/2009 | Werneth et al. |
| 2009/0275940 A1 | 11/2009 | Malackowski et al. |
| 2010/0241115 A1 | 9/2010 | Benamou et al. |
| 2010/0241116 A1 | 9/2010 | Benamou et al. |
| 2010/0324550 A1 | 12/2010 | Morgan et al. |
| 2010/0331666 A1 | 12/2010 | Wallace |
| 2011/0178515 A1 | 7/2011 | Bloom et al. |
| 2011/0270237 A1 | 11/2011 | Werneth et al. |
| 2012/0095457 A1 | 4/2012 | Morgan et al. |
| 2012/0136346 A1 | 5/2012 | Condie et al. |
| 2012/0136347 A1 | 5/2012 | Brustad et al. |
| 2012/0136348 A1 | 5/2012 | Condie et al. |
| 2012/0157985 A1 | 6/2012 | Ballou et al. |
| 2012/0197243 A1 | 8/2012 | Sherman et al. |
| 2012/0215216 A1 | 8/2012 | Friedrichs et al. |
| 2012/0265196 A1 | 10/2012 | Turner et al. |
| 2013/0053840 A1 | 2/2013 | Krapohl et al. |
| 2013/0253502 A1 | 9/2013 | Aronow et al. |
| 2013/0274729 A1 | 10/2013 | Orszulak |
| 2014/0018795 A1 | 1/2014 | Shiley et al. |
| 2014/0025061 A1 | 1/2014 | Benamou |
| 2014/0039517 A1 | 2/2014 | Bowling et al. |
| 2014/0052123 A1 | 2/2014 | Benamou et al. |
| 2014/0200621 A1 | 7/2014 | Malackowski et al. |
| 2014/0232316 A1 | 8/2014 | Philipp |
| 2014/0276750 A1 | 9/2014 | Gilbert |
| 2014/0276754 A1 | 9/2014 | Gilbert et al. |
| 2014/0276768 A1 | 9/2014 | Juergens et al. |
| 2014/0324039 A1 | 10/2014 | Malackowski et al. |
| 2015/0088118 A1 | 3/2015 | Gilbert et al. |
| 2015/0230861 A1 | 8/2015 | Woloszko et al. |

OTHER PUBLICATIONS

Force 4 Service Manual, May 1, 1985, Valleylab Part No. A945 100 055A, pp. 1-144.

PCT International Search Report dated Jan. 27, 2017, 4 pages.

\* cited by examiner

FINGERSWITCH CIRCUITRY TO REDUCE RF LEAKAGE CURRENT

CROSS-REFERENCE TO RELATED APPLICATION

This application is related to and claims priority to U.S. Provisional Patent Application Ser. No. 62/073,705, filed Oct. 31, 2014, entitled COMBINATION PEAK PLASMA AND TRANSCOLLATION TIP, and claims priority to U.S. Provisional Patent Application Ser. No. 62/164,930, filed May 21, 2015, entitled ELECTROSURGICAL GENERATOR the entirety of which is incorporated herein by reference.

STATEMENT REGARDING FEDERALLY SPONSORED RESEARCH OR DEVELOPMENT n/a

TECHNICAL FIELD

The present invention relates to an electrosurgical unit having a radiofrequency generator, and in particular, detection circuitry configured to multiplex signals from an electrosurgical hand piece and to reduce radiofrequency leakage current.

BACKGROUND

Electrosurgery is the application of radio frequency electrical energy to biological tissue to cut, coagulate, desiccate, or fulgurate tissue. Electrosurgical units typically include an electrosurgical generator configured to supply the electrical energy, and an electrosurgical hand piece configure to electrically couple with the electrosurgical unit and deliver the electrical energy to the tissue. To determine the desired electrical energy requested by the user of the hand piece, the electrosurgical unit may include one or more energized detection circuits that are configured to transmit energy requests from the electrosurgical hand piece to the electrosurgical generator, which is configured to supply electrosurgical energy to the electrosurgical hand piece. The energized detection circuit typically includes one or more detection circuits that electrically couple to one or more finger switches on the electrosurgical hand piece.

Presently, each finger switch on the electrosurgical hand piece includes an associated isolation transformer as part of the energized detection circuits. For example, an electrosurgical hand piece including three finger switches for three different power modes would typically include at least three isolation transformers in the energized detection circuit. However, radiofrequency leakage current, which is inadvertent electrical current between the electrosurgical unit and the ground, is related to the number of electrical components across the isolation barrier between the electrosurgical unit and the patient. Radiofrequency leakage current can harm the patient by causing patient burns, thus it is desirous to minimize leakage current. Because leakage current is related to parasitic capacitance across the transformers, the more transformers across the isolation barrier the more leakage current.

SUMMARY

The present invention advantageously provides for an electrosurgical unit having detection circuitry for reducing radiofrequency leakage current in an electrosurgical unit. The electrosurgical unit includes a radiofrequency generator configured to generate electrosurgical energy, the radiofrequency generator including a detection circuit having a resistor ladder and an isolation transformer in electrical communication with the resistor ladder. The detection circuit is configured to detect a change in impedance across the isolation transformer and correlate the change in impedance to one of a plurality of predetermined energy thresholds.

In another embodiment, the electrosurgical unit includes a radiofrequency generator configured to generate electrosurgical energy. The radiofrequency generator includes a detection circuit having a plurality of finger switch conductors. Each of the plurality of finger switch conductors is configured to be in electrical communication with a corresponding finger switch on an electrosurgical hand piece. Each finger switch has an open position and a closed position. Each of the plurality of finger switch conductors including at least one resistor, the at least one resistor in each of the plurality of finger switch conductors collectively defining a resistor ladder. An isolation transformer in electrical communication with the plurality of finger switch conductors and the resistor ladder is included. The detection circuit is configured to detect a change in impedance across the isolation transformer when any one of the corresponding finger switches is placed in the closed position.

In yet another embodiment, the electrosurgical unit includes a radiofrequency generator configured to generate electrosurgical energy. The radiofrequency generator includes a detection circuit having three finger switch conductors. Each of the three finger switch conductors are configured to be in electrical communication with a corresponding finger switch on an electrosurgical hand piece, each finger switch has an open position and a closed position. Each of the three finger switch conductors includes at least one load resistor, the at least one load resistor in each of the plurality of finger switch conductors collectively defining a resistor ladder and having a different resistance than any other load resistors. An isolation transformer in electrical communication with the three finger switch conductors and the resistor ladder is included. A first radiofrequency oscillator configured to generate radiofrequency energy at a first frequency is included, the radiofrequency generator further includes a second radiofrequency oscillator configured to generate radiofrequency energy at a second frequency greater than the first frequency. A current sensing resistor is disposed between the first radiofrequency oscillator and the isolation transformer, the current sensing resistor is configured to measure a change in current across the isolation transformer. A difference amplifier is in communication with the current sensing resistor. A Sallen key filter is in communication with the difference amplifier. The detection circuit is configured to detect a change in impedance across the isolation transformer when any one of the corresponding finger switches is placed in the closed position and to correlate the change in impedance to one of a plurality of predetermined energy thresholds, the plurality of predetermined energy thresholds includes at least four predetermined energy thresholds, and each of the four predetermined energy thresholds includes a 12 bit ADC value.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

As used here, relational terms, such as "first" and "second," "top" and "bottom," "front and rear," and the like, may be used solely to distinguish one entity or element from another entity or element without necessarily requiring or implying any physical or logical relationship or order between such entities or elements.

Figure 1:
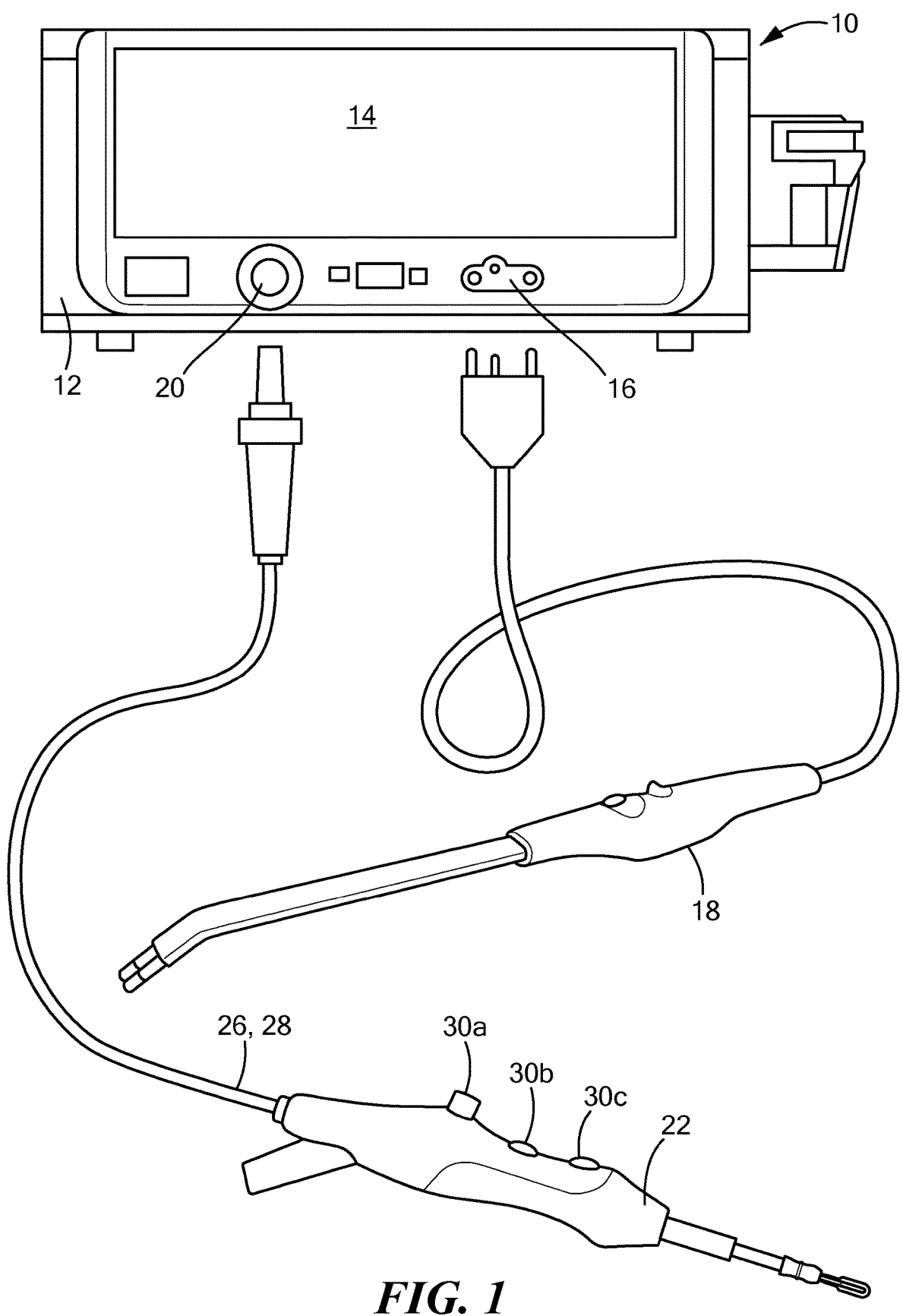
FIG. 1 is a front perspective view of an electrosurgical hand piece and electrosurgical unit constructed in accordance with the principles of the present application.

Referring now to the drawings in which like reference designators refer to like elements, there is shown in FIG. 1 and exemplary electrosurgical unit ("ESU") constructed in accordance with the principles of the present application and designated generally as "10." The ESU 10 may include a radiofrequency generator 12 configured to house and electrically couple the components and circuits of the ESU 10, and a touch actuated display 14 configured to receive energy requests from one or more electrosurgical hand pieces that electrically couple to the radiofrequency generator 12, display treatment progress and measurements, for example, impedance, and initiate and/or terminate the supply of radiofrequency energy and fluid for one or more electrosurgical hand pieces that may be electrically coupled to the ESU 10. In an exemplary configuration, the ESU 10 includes a first receptacle 16, which may be a 3-pin connector configured to receive and electrical couple with a first electrosurgical hand piece 18 configured to deliver bipolar radiofrequency energy to tissue. The ESU 10 may further include a second receptacle 20, for example, a 7-pin receptacle, configured to receive and electrically couple with a second electrosurgical hand piece 22 configured to deliver at least one of monopolar radiofrequency energy or a combination of bipolar radiofrequency energy and monopolar radiofrequency energy. In an exemplary configuration, the second electrosurgical hand piece 22 is an electrosurgical hand piece constructed in accordance with the principles of the electrosurgical hand piece disclosed in pending U.S. application Ser. No. 14/688,723 entitled TELESCOPING DEVICE WITH SALINE IRRIGATION LINE, the entirety of which is expressly incorporated herein by reference.

The second electrosurgical hand piece 22 may include a handle 24 which includes a first umbilical 26 fluidly coupled to a fluid source, such as saline, (not shown) and a second umbilical 28 electrically coupling the second electrosurgical hand piece 22 to the ESU 10. Both the first umbilical 26 and the second umbilical 28 may be coupled to the ESU 10 via separate portions or may combined into a single plug connected to the ESU 10. The handle 24 may further include a first finger switch 30a configured to operate the second electrosurgical hand piece 22 in CUT mode, which applies a maximum voltage in the range of approximately 500V to 1250V, at a duty cycle of approximately 0.2% to 100% (depending on the burst duration, which may range from approximately 7 to 80 microseconds), and at a frequency of approximately 0.4 MHz; a second finger switch 30b, configured to operate the second electrosurgical hand piece 22 in COAG mode, which applies a maximum voltage in the range of approximately 700V to 2600V, at a duty cycle of approximately 6-44% (depending on the burst duration, which may range from approximately 5-40 microseconds), and at a frequency of approximately 0.4 MHz; and a third finger switch 30c configured to operate the second electrosurgical hand piece 22 in TRANS mode, which may apply similar voltages, frequencies, and duty cycles to that of pure CUT mode or may be configured to output bipolar radiofrequency energy to coagulate with saline. Actuation of the third finger switch 30c is also configured to initiate the flow of saline at a constant, adjustable, or variable flow rate toward the distal end of the second electrosurgical hand piece 22.

Figure 2:
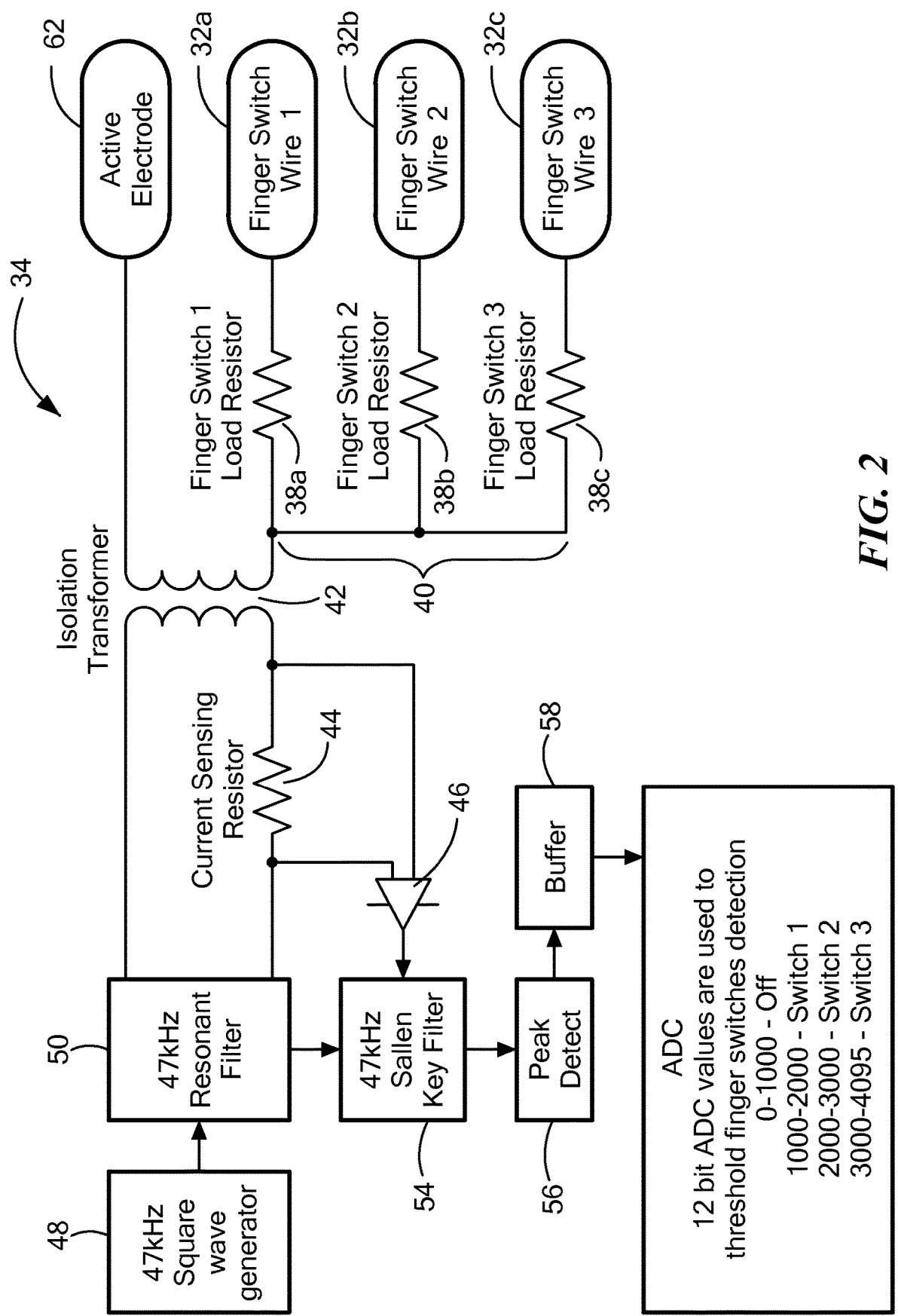
FIG. 2 is a schematic of a detection circuit of the electrosurgical hand piece shown in FIG. 1.

Now referring to FIG. 2, each of the finger switches 30 may include a corresponding finger switch conductor 32 which electrically couples to the corresponding finger switch 30. For example, a first finger switch conductor 32a, which may be for example a wire, may electrically couple with finger switch 30a; a second finger switch conductor 32b may electrically couple with the second finger switch 30b; and a third finger switch conductor 32c may electrically couple with the third finger switch 30c. The finger switch conductors 32 may extend from, for example, the second receptacle 20 into the circuitry of the radiofrequency generator 12, and in particular into a detection circuit 34 of the radiofrequency generator 12. The detection circuit 34 is configured to multiplex energy request signals relayed from the finger switches 30 through corresponding finger switch conductors 32 when a respective finger switch 30 is actuated, to determine the energy requested by the second electrosurgical hand piece 22. The requested energy information may then be relayed to a radiofrequency output source 36 within the radiofrequency generator 12 configured to provide radio frequency energy to the second electrosurgical hand piece 22.

In an exemplary configuration, the detection circuit 34 includes the finger switch conductors 32 arranged in parallel. Each of the finger switch conductors 32 includes a corresponding load resistor 38. In particular, finger switch conductor 32a includes a first load resistor 38a; the second finger switch conductor 32b includes a second load resistor 38b; and the third finger switch conductor 32c includes a third load resistor 38c. The load resistors 38 form a resistor ladder 40. Although three load resistors 38 are illustrated as forming the resistor ladder 40, it is contemplated that where only two finger switch conductors are included, for example, in a configuration in with one or the first and second electrosurgical hand pieces includes two finger switches, only two resistors may define the resistor ladder 40. In one configuration, each load resistor 38 has the same resistance, and in other configuration each load resistor 38 has a different resistance than any other load resistor 38 in the resistor ladder 40.

The resistor ladder 40 is electrically coupled to an isolation transformer 42 configured to isolate a supply of radiofrequency energy between the ESU 10 and the one or more electrosurgical hand pieces 18 and 22. In the particular configuration shown in FIG. 2, the isolation transformer 42 electrically isolates the second electrosurgical hand piece 22 from the ESU 10. In this configuration, the secondary winding of the isolation transformer 42 is electrically coupled to the resistor ladder 40. In particular, whether the resistor ladder 40 includes two or more load resistors, a single isolation transformer 42 is included, which reduces the total number of isolation transformers typically used in the ESU 10. In particular, prior art multi finger switch electrosurgical hand pieces associate at least three isolation transformers for a three finger switch electrosurgical hand piece, which raises the overall parasitic capacitance across the isolation barrier and increases the radiofrequency leakage current. By reducing the number of isolation transformers in half, approximately half the capacitance, and thus half the leakage current, is produced. Any number of finger switches 30 and associated finger switch conductors 32 may be added without increasing the number of isolation transformers. Thus, an electrosurgical hand piece having "n" number of finger switches 30 electrically coupled to the detection circuit 40 constructed in accordance with the principles describe above, would include a single corresponding isolation transformer 42 in the detection circuit 40.

Figure 3:
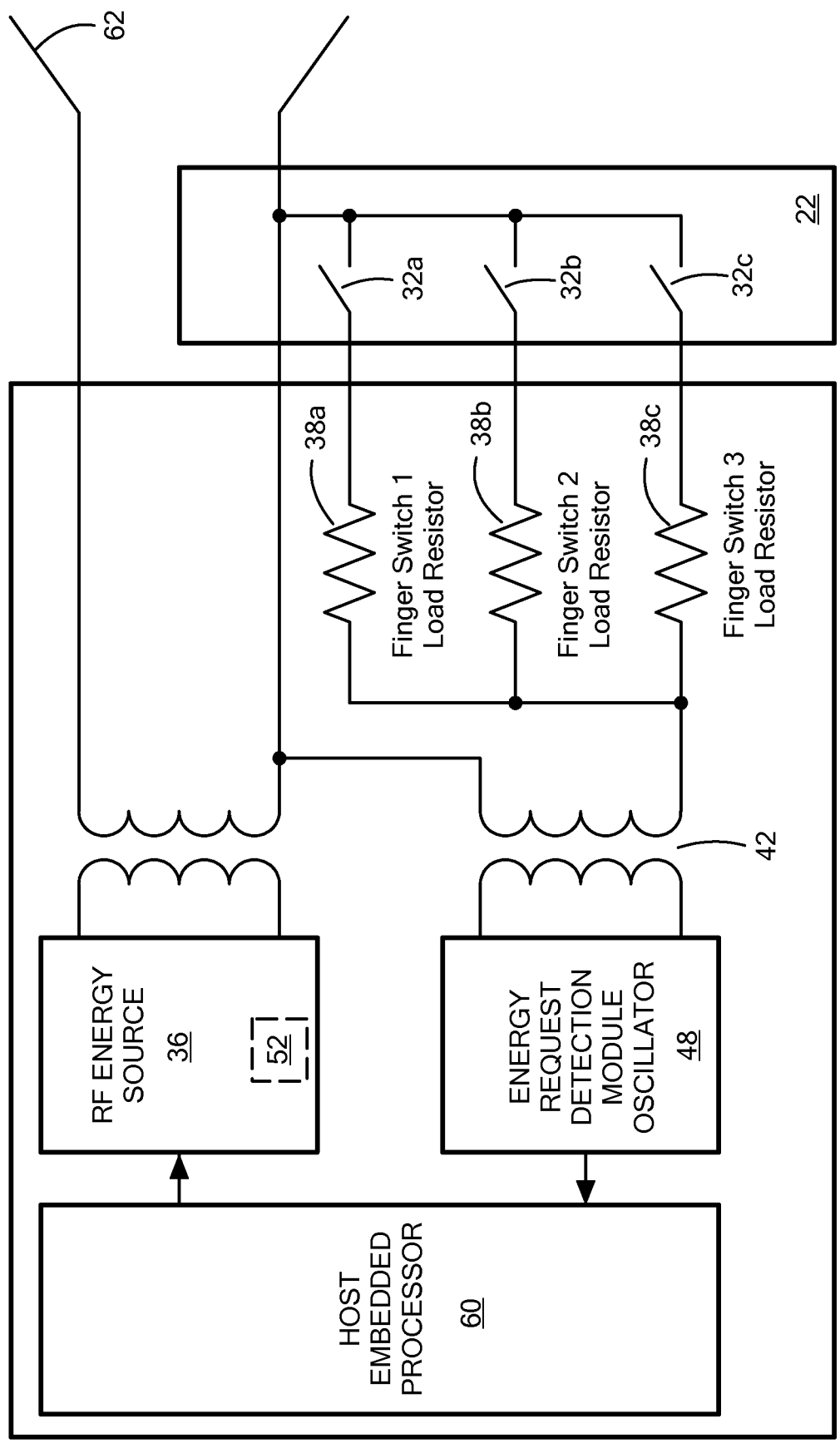
FIG. 3 is a schematic of the detection circuit shown in FIG. 2 in communication with a radiofrequency generator of the electrosurgical unit shown in FIG. 1.

Referring now to FIGS. 2 and 3, the primary winding of the isolation transformer 42 may be electrically coupled to a current sensing resistor 44. The current sensing resistor 44 is a low resistance resistor configured to sense the current flowing through it the form of a voltage drop, which can be detected and amplified. In particular, the current sensing resistor 44 may be coupled to a difference amplifier 46, and other components discussed in more detail below, configured to detect a change in voltage or current across the resistor 44 as a result one of the finger switches 30 being depressed. Upstream of the current sensing resistor 44 is a first radiofrequency oscillator 48 configured to generate a radiofrequency signal and a resonant filter 50 configured to filter the waveform generated by the first radiofrequency oscillator 48 at the same frequency as the waveform. In an exemplary configuration, the first radiofrequency oscillator 48 generates a square waveform at 47 kHz which provides power to the detection circuit 40 after being converted to a sine save by the resonant filter 50. In contrast, the radiofrequency output source 36 includes a second radiofrequency oscillator 52 configured to generator a radiofrequency waveform at approximately in the range of 400 kHz to 500 khz to provide power to at least one of the first and second electrosurgical devices 18 and 22. In an exemplary configuration, the second radiofrequency oscillator 52 generates a waveform at a single frequency of 473 kHz. Thus, the second radiofrequency oscillator 52 generates a radiofrequency waveform approximately 10 times greater than the radiofrequency waveform of the first radiofrequency oscillator 48, which prevents un-differentiable interference between the two oscillators.

Continuing to refer to FIGS. 2 and 3, when the user of, for example, the second electrosurgical hand piece 22 depresses one of the finger switches 30, the circuit between the depressed finger switch and the isolation transformer 42 is shorted and a pathway is created for the flow of current across the isolation transformer 40 as a function of the resistance of its corresponding load resistor. For example, each of the finger switches 30 has an open position in which current does not flow across the isolation transformer 40. When one of the finger switches 30 is depressed into a closed position, the isolation transformer 40 is shorted such that a pathway for current to flow by inductance across the isolation transformer 40 is created from the first radiofrequency oscillator 48, across the isolation transformer 40, through the respective finger switch conductor 32, and through the load resistors 38. The current across the isolation transformer 40 is a function of the respective load resistor 38. Thus, the current sensing resistor 44 can measure this current and calculate a voltage drop across the current sensing resistor 44. In particular, the difference amplifier 46 can amplify the voltage drop across the current sensing resistor 44. The amplified voltage drop can then be filtered by a filter 54. For example, the filter 54 may be a Sallen Key Filter, which is an electronic filter topology configured to implement a second-order active filter. The peak of the filtered voltage drop may then be detected with a peak detector 56 and signal processed by a buffer 58. The buffered voltage drop signal may then be assigned a predetermined energy threshold value, which is then correlated to the particular finger switch 30 that is depressed. For example, four 12 bit ADC predetermined energy threshold values may be assigned to each of the finger switches 30. For example, a value of 0-1000 indicates that no finger switch 30 has been depressed. A value between 1000-2000 indicates finger switch 30a has been depressed, a value between 2000-3000 indicates finger switch 30b has been depressed, and a value between 3000-4095 indicates that finger switch 30 has been depressed. The assigned predetermined threshold values may then be communicated to a one or more processors 60, which in turn communicates with the radiofrequency output source 36 to provide a determined radiofrequency waveform based on which finger switch has been depressed. This waveform may then be transmitted to the active electrode 62 for treatment of tissue.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An electrosurgical unit, comprising:
   a radiofrequency generator configured to generate electrosurgical energy, the radiofrequency generator including a detection circuit, the detection circuit having:
   a resistor ladder having at least three resistors;
   a single isolation transformer in electrical communication with the resistor ladder; and
   the detection circuit being configured to detect a change in impedance across the isolation transformer and correlate the change in impedance to one of a plurality of predetermined energy thresholds.

2. The electrosurgical unit of claim 1, wherein the detection circuit includes a plurality of finger switch conductors, and wherein each resistor in the resistor ladder is a load resistor electrically coupled to a corresponding one of the plurality of finger switch conductors.

3. The electrosurgical unit of claim 2, wherein each resistor in the resistor ladder has a different resistance than any other resistor in the resistor ladder.

4. The electrosurgical unit of claim 1, wherein the detection circuit further includes a first radiofrequency oscillator configured to generate radiofrequency energy at a first frequency, and wherein the radiofrequency generator includes a second radiofrequency oscillator configured to generate radiofrequency energy at a second frequency greater than the first frequency.

5. The electrosurgical unit of claim 4, wherein the first radiofrequency oscillator is in electrical communication with the isolation transformer.

6. The electrosurgical unit of claim 5, wherein the detection circuit includes a current sensing resistor disposed between the first radiofrequency oscillator and the isolation transformer, the current sensing resistor being configured to measure a change in current across the isolation transformer.

7. The electrosurgical unit of claim 6, wherein the current sensing resistor is in communication with a difference amplifier.

8. The electrosurgical unit of claim 7, wherein the difference amplifier is in communication with a Sallen key filter.

9. The electrosurgical unit of claim 1, wherein the plurality of predetermined energy thresholds includes at least four predetermined energy thresholds, and wherein each of the four predetem lined energy thresholds includes a 12 bit ADC value.

10. An electrosurgical unit, comprising:

a radiofrequency generator configured to generate electrosurgical energy, radiofrequency generator including a detection circuit, the detection circuit having:

three finger switch conductors, each of the three finger switch conductors being configured to be in electrical communication with a corresponding finger switch on the electrosurgical hand piece, each finger switch having an open position and a closed position;

each of the three finger switch conductors including at least one load resistor, the at least one load resistor in each of the three finger switch conductors collectively defining a resistor ladder and having a different resistance than any other load resistors;

a single isolation transformer in electrical communication with the three finger switch conductors and the resistor ladder;

a first radiofrequency oscillator configured to generate radiofrequency energy at a first frequency, the radiofrequency generator including a second radiofrequency oscillator configured to generate radiofrequency energy at a second frequency greater than the first frequency;

a current sensing resistor disposed between the first radiofrequency oscillator and the isolation transformer, the current sensing resistor being configured to measure a change in current across the isolation transformer;

a difference amplifier in communication with the current sensing resistor;

a Sallen key filter in communication with the difference amplifier; and the detection circuit configured to detect a change in impedance across the isolation transformer when any one of the corresponding finger switches is placed in the closed position and to correlate the change in impedance to one of a plurality of predetermined energy thresholds, the plurality of predetermined energy thresholds including at least four predetermined energy thresholds, and wherein each of the four predetermined energy thresholds includes a 12 bit ADC value.

* * * * *